United States Patent [19]

Wright

[11] 4,007,009
[45] Feb. 8, 1977

[54] CHEMICAL ANALYSIS OF IONS INCORPORATED IN LATTICES USING COHERENT EXCITATION SOURCES

[75] Inventor: John C. Wright, Oregon, Wis.

[73] Assignee: Wisconsin Alumni Research Foundation, Madison, Wis.

[22] Filed: Feb. 11, 1976

[21] Appl. No.: 657,252

[52] U.S. Cl. .............................. 23/230 R; 250/458
[51] Int. Cl.² .................... G01J 1/58; G01N 33/18
[58] Field of Search .......... 23/230 R; 250/458, 461

[56] References Cited
UNITED STATES PATENTS 3,445,656  5/1969  Hull et al. ........................ 250/461
3,793,527  2/1974  Forest ........................... 250/461 X OTHER PUBLICATIONS
Talant et al., J. Chem. Phys. 63, 2074 (1975).

Primary Examiner—Robert M. Reese
Attorney, Agent, or Firm—McDougall, Hersh & Scott

[57] ABSTRACT

Method for analysis of cations and anions in trace amounts in solution by excitation with a tuneable laser of a precipitate or a coprecipitate formed of the unknown ions in the presence of ions which fluoresce upon excitation by the dye laser and which experience change in energy levels in the presence of the unknown ion in the crystalline lattice.

15 Claims, 6 Drawing Figures

CHEMICAL ANALYSIS OF IONS INCORPORATED IN LATTICES USING COHERENT EXCITATION SOURCES

The Government has rights in this invention pursuant to Grant No. MPS-74-24394 and IPA No. 0001 awarded by the National Science Foundation.

This invention relates to a procedure for the determination of ions present in solution in concentrations which may go as low as trace concentration levels, and it relates more particularly to a procedure in which ions, both cation and anion, and the amounts thereof in solution can be determined in a simple and efficient manner, even when such cations or anions are present in trace amounts.

There is a growing need for analytical procedures for determining the presence of ions in solution, such as in the water in the waterways of the world, underground water and the like, as well as the effluent from plants and equipment, including fall-out from nuclear explosions, nuclear fission and the like. Very often such ions are present only in such trace amounts as to defy detection. The need for analysis extends to vapor and solid effluent from the stacks of most industrial operations, such as in the generation of power, production of paper, plastics, steel, hydrocarbon and other organic or inorganic chemicals, metallurgical operations, and the like, and more particularly in the liquid waste from such operations which are often dissipated into the ground, bodies of water, or into the atmosphere, and which might contain heretofore undetectable amounts of pollutants.

It is an object of this invention to provide a new and improved method for ion analysis in which the ion, either cation or anion, can be determined even when present in trace concentration levels; in which the concentration of such ions in solution can be relatively accurately estimated; in which the procedure makes use of existing and readily available materials and equipment; and in which the determination can be made in a simple and efficient manner, on a relatively routine basis, without the need for highly skilled labor.

These and other objects and advantages of this invention will hereinafter appear, and for purposes of illustration, but not of limitation, an embodiment of the invention is shown in the accompanying drawings in which FIG. 1 is an excitation spectrum obtained by low resolution monitoring of fluorescence from all sites simultaneously at 620 nm as the dye laser wavelength is scanned over all possible excitation wavelengths from $^7F_0 \rightarrow {}^5D_o$ transitions around 570 nm;

Figure 1:
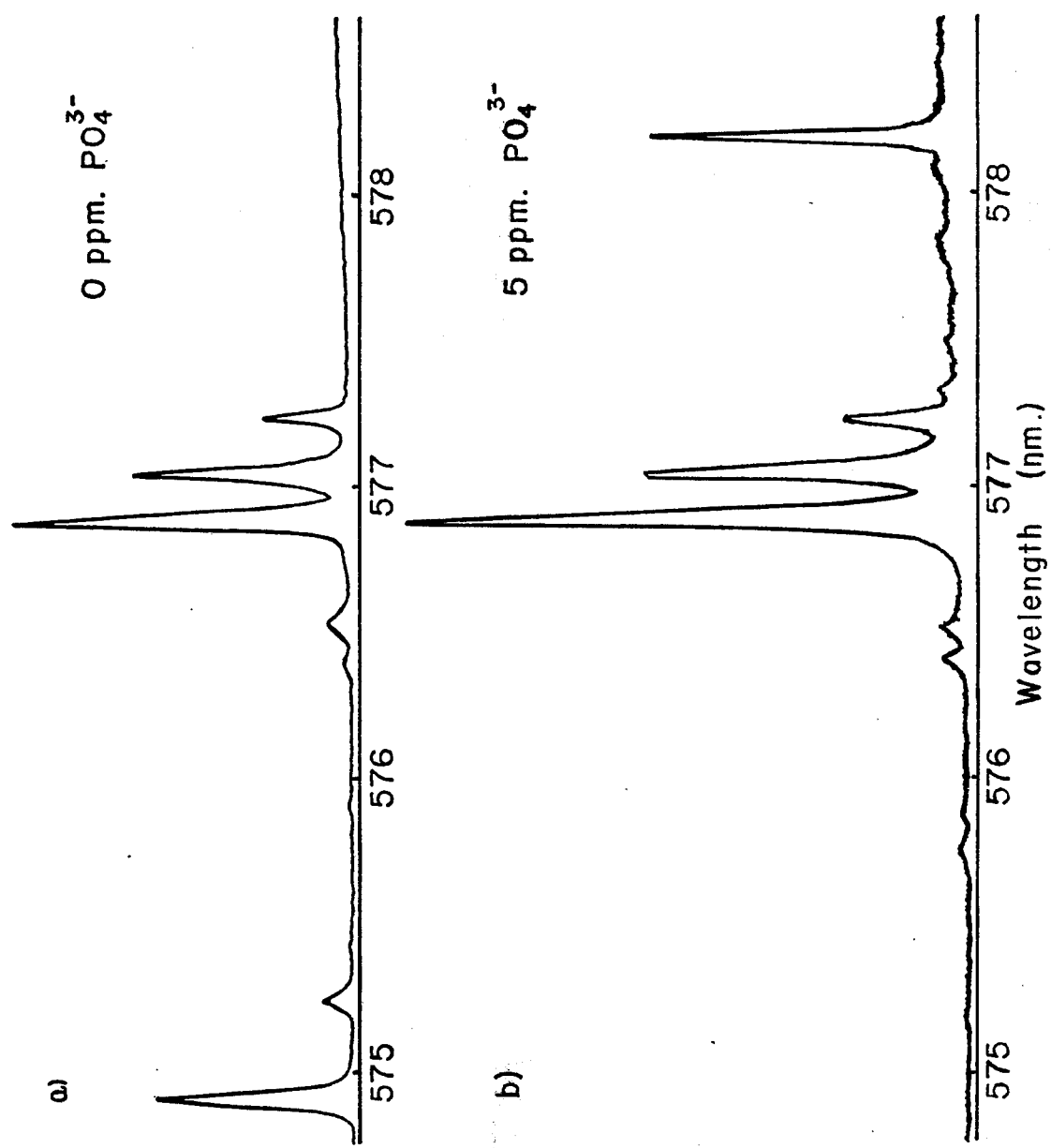

Theoretical explanation of the practice of the technique of this invention and its many ramifications will be described after introduction of the invention by way of the following example addressed to the analysis of a solution containing phosphate ion $PO_4^{---}$ in trace amounts.

A 0.10 M solution of sodium sulphate ($Na_2SO_4$) in water is prepared. In a separate container, a 0.10 M solution in water of barium chloride ($BaCl_2$) is prepared. A dilute solution of europium chloride ($EuCl_3$) is added to the $BaCl_2$ solution in the ratio of 5 ml of a $2 \times 10^{-3}$ molar solution in water of $EuCl_3$ per 200 ml of the $BaCl_2$ solution.

A 50 ml aliquot of the 0.10 M $Na_2SO_4$ solution is taken in a beaker and a solution containing trace amounts of phosphate ($PO_4^{---}$) in solution is added to it. Alternatively, the $Na_2SO_4$ solution may be prepared from a phosphate containing solution.

40 ml of the $BaCl_2$—$EuCl_3$ solution is then added slowly with constant stirring to the $Na_2SO_4$ solution over an 8 minute period with the precipitation of barium sulphate (the latter time is not critical). Nor is temperature significant since the solution can be at room temperature or above. The solutions are then heated to allow aging of the $Ba_2SO_4$ precipitate thus formed. Following aging, the precipitates are washed, filtered or decanted, and then dried at a low temperature (about 120° C). The dried powder can then be transferred to small recessed holes in the sample holder and pressed into pellets for mounting in a cryogenic refrigerator. Alternatively, the dried powder can be transferred to platinum crucibles and ignited in a high temperature furnace (400°–1100° C). The ignited powder can then be ground and transferred to the sample holder to be pressed into pellets.

In order to perform a quantitative analysis, a standard phosphate containing precipitate must be used in conjunction with the samples containing unknown amounts of phosphate to calibrate the apparatus. Provisions are made in the sample holder for the mounting of additional pellets which can serve as standards for the calibration.

The sample holder is mounted on a cryogenic refrigerator and cooled to low temperature (the measurement can also be performed at room temperature). A dye laser is used to excite fluorescence from the $Eu^{3+}$ containing $BaSO_4$. The excitation wavelength that is used corresponds to the absorption wavelength of $Eu^{3+}$ and can correspond with transitions from the ground state of $Eu^{3+}$ to the $^5D_o$, $^5D_1$, $^5D_2$, or any of the higher manifolds. Use was made of transitions to the $^5D_2$ and $^5D_o$ manifolds (about 464 nm and 577 nm respectively). The resulting fluorescence can be detected with a low resolution monochromator such as a ¼ m Jarrell-Ash instrument if a number of sites are observed simultaneously or with a high resolution instrument such as a 1 m Interactive Technology instrument if individual sites are monitored. Any of the known $Eu^{3+}$ fluorescent transitions can be monitored. Use was made of a photomultiplier with S-20 or one with S-5 response to observe the fluorescence. A current-to-voltage converter and a gated integrator is used to obtain a d.c. voltage output proportional to the fluorescence intensity. The output is displayed on a strip chart recorder.

Figure 2:
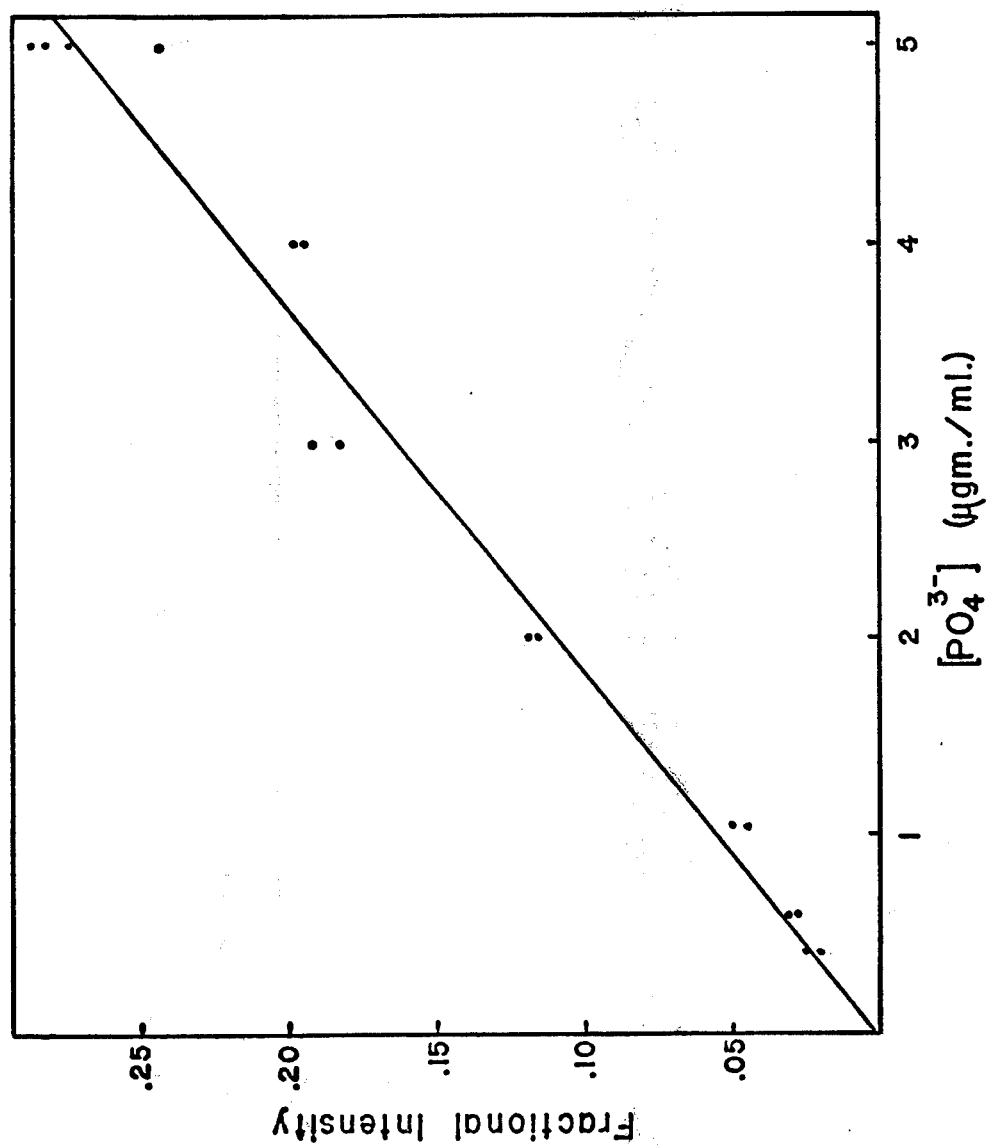
FIG. 2 is a curve showing the relation of intensity in amount of $PO_4^{---}$ in solution.
Figure 3:
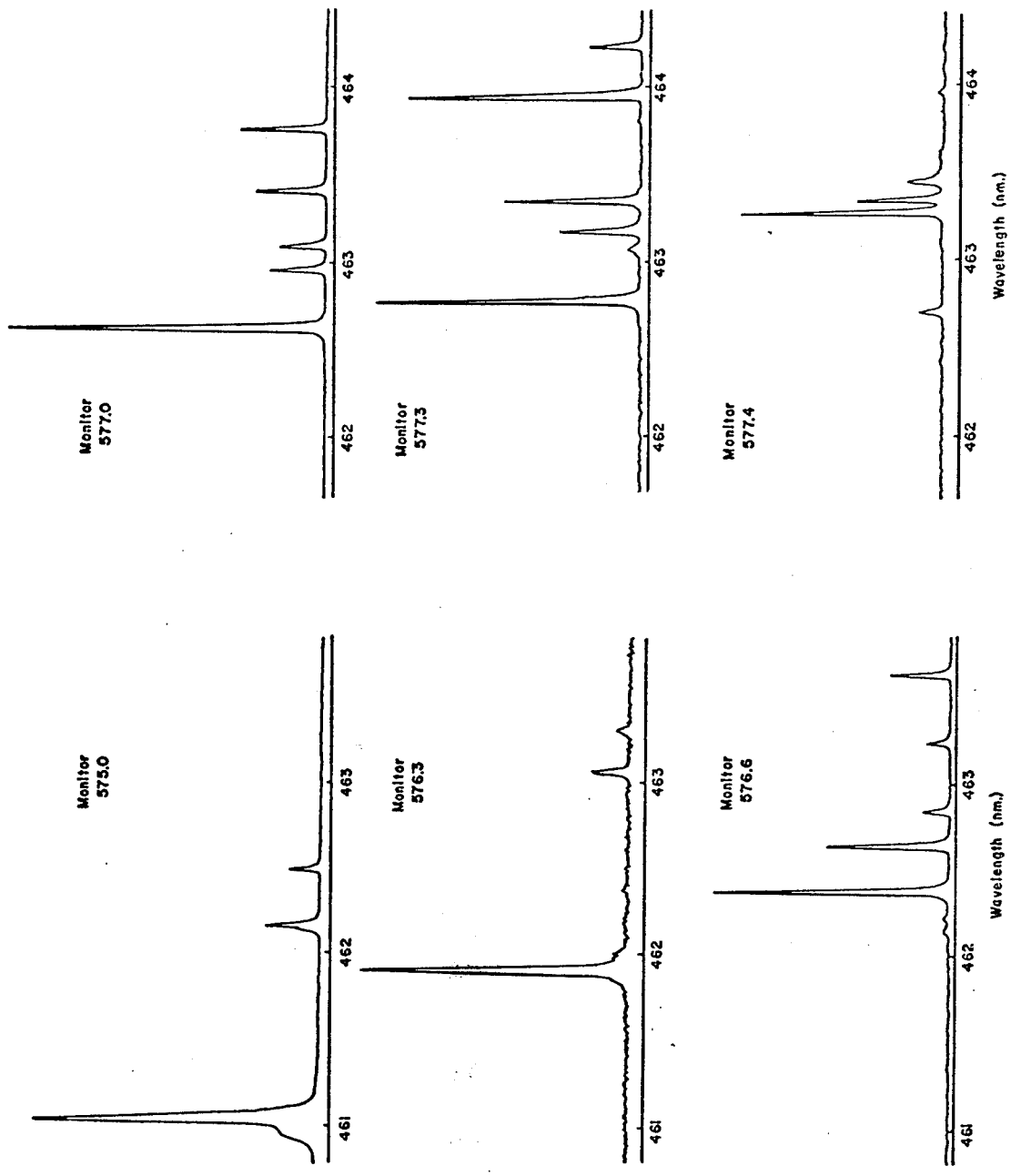
FIG. 3 shows the selective excitation spectra for $^5D_o \rightarrow {}^7F_o$ fluorescence while exciting the $^5D_2$ manifold for six of the 13 major intrinsic sites in $BaSO_4$, with each spectra arising from a single site.
Figure 4:
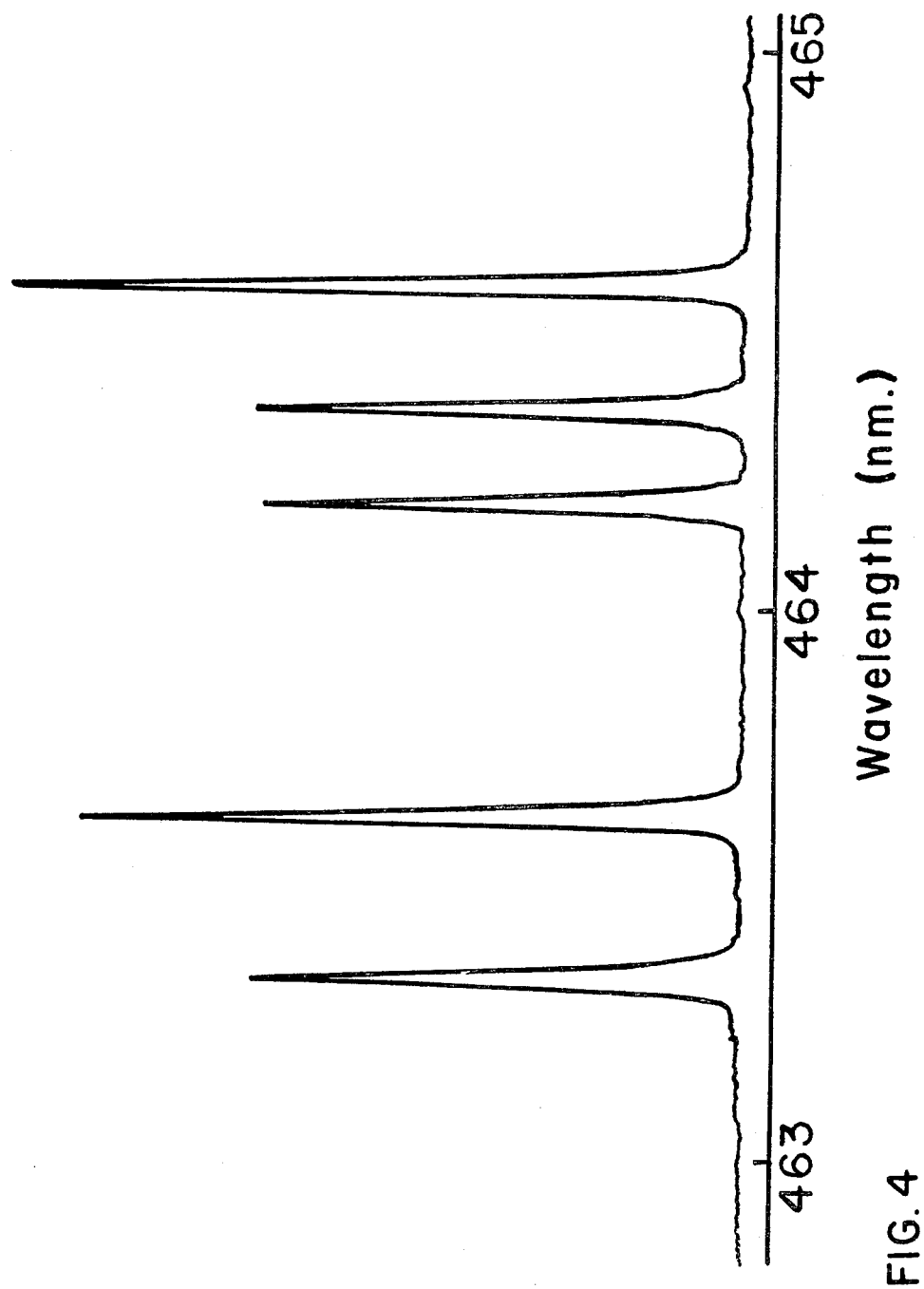
FIG. 4 shows the spectrum obtained at 3 ppm $PO_4^{---}$ concentration in solution before precipitation; no such lines appear in precipitations in the absence of $PO_4^{---}$.

Typical results are shown in the accompanying figures. FIG. 1 shows the excitation spectrum that is obtained by low resolution monitoring of fluorescence from all sites simultaneously at 620 nm as the dye laser wavelength is scanned over all possible excitation wavelengths from the $^7F_o \rightarrow {}^5D_o$ transitions around 570 nm. Each line represents one site. The line at 578.2 nm is associated with the introduction of $PO_4^{---}$ into the sample. Its intensity is related to the amount of $PO_4^{---}$ in the original solution as can be seen from FIG. 2. If each of the lines shown in FIG. 1 is monitored in fluorescence with a high resolution instrument, one obtains single site excitation spectra. These results are shown in FIG. 3 for representative lines of FIG. 1. This figure was obtained by scanning the dye laser wavelength over all possible excitation wavelengths of the $^7F_o \rightarrow {}^5D_2$ transition. For each site, one would expect 5 lines as one sees for a number of the sites in FIG. 3. The excitation spectrum for the $PO_4^{---}$ site at 578.2 nm is shown in FIG. 4. It is being excited alone without contribution from any other site.

Figure 5:
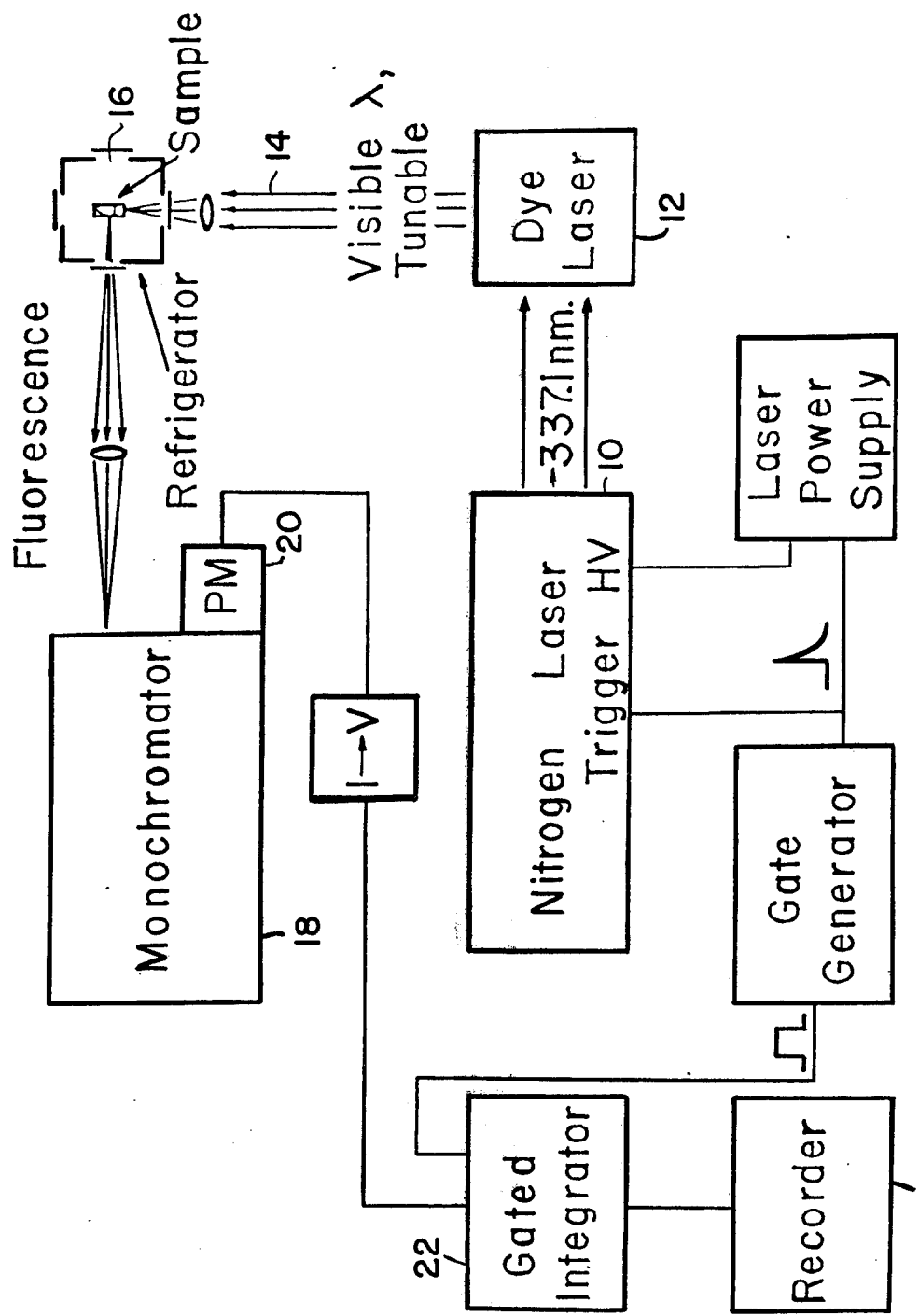
FIG. 5 is a diagram of the apparatus used selectively to excite fluorescence in accordance with the practice of this invention.

The dye laser, used to excite fluorescence from the europium containing $BaSO_4$ precipitate, is illustrated in FIG. 5 in which the Molectron nitrogen laser 10 is used to pump a dye laser 12. This configuration is capable of scanning over wide wavelength regions throughout the visible, with excellent reliability. A telescope is inserted into the dye laser cavity to achieve a band width of about 0.01 nm. The output beam 14 is directed to the sample 16 mounted on a cryogenic refrigerator (from Air Products) to cool the sample to 10 K. The fluorescence from the sample is analyzed with a 1 meter monochromator 18 of Czerny-Turner design. An EMI 9658 photomultiplier 20 is used with a gated integrator 22 for detection, with the signals transmitted to a recorder 24.

A conventionally obtained fluorescence spectrum of a correspondingly prepared precipitate without $PO_4^{---}$ in solution from which it is prepared, revealed only broad, intense bands without appreciable structure that could be used to characterize particular sites. However, when, in accordance with an important concept of this invention, use is made of a dye laser selectively to excite the precipitate, sharp line fluorescence is obtained. The spectrum of this precipitate identifies 13 major sites that appear to be intrinsic to the lattice under the precipitation conditions used. Each of the sites can be selectively excited from the others. The excitation spectra for six of these sites are shown in FIG. 3.

When, as in Example 1, $PO_4^{---}$ are introduced into the $Na_2SO_4$ solution from which the $BaSO_4$ is precipitated, a new site appears in the spectrum which can also be selectively excited.

The excitation spectrum for this site is shown in FIG. 4 for a concentration of three parts per million (ppm) concentration of $PO_4^{---}$ in the original solution. Each of the lines in this figure arise only from the $PO_4^{---}$ site. In this way it has been possible to measure $PO_4^{---}$ concentration in solution at levels as low as 200 parts per billion (ppb) and there is reason to believe that the procedure is effective to measure $PO_4$ concentration levels at least two orders of magnitude lower. The intensity of the lines are linearly related to the $PO_4$ concentration in the original solution thereby not only to give a qualitative analysis but also a quantitative analysis.

The series of concepts that are involved in this procedure for trace analysis, as hereinafter described, will indicate the scope to which this invention can be applied in the analysis and evaluation of anions and cations present in solution in amounts as low as trace levels, or levels which have heretofore defied detection and estimation.

Figure 6:
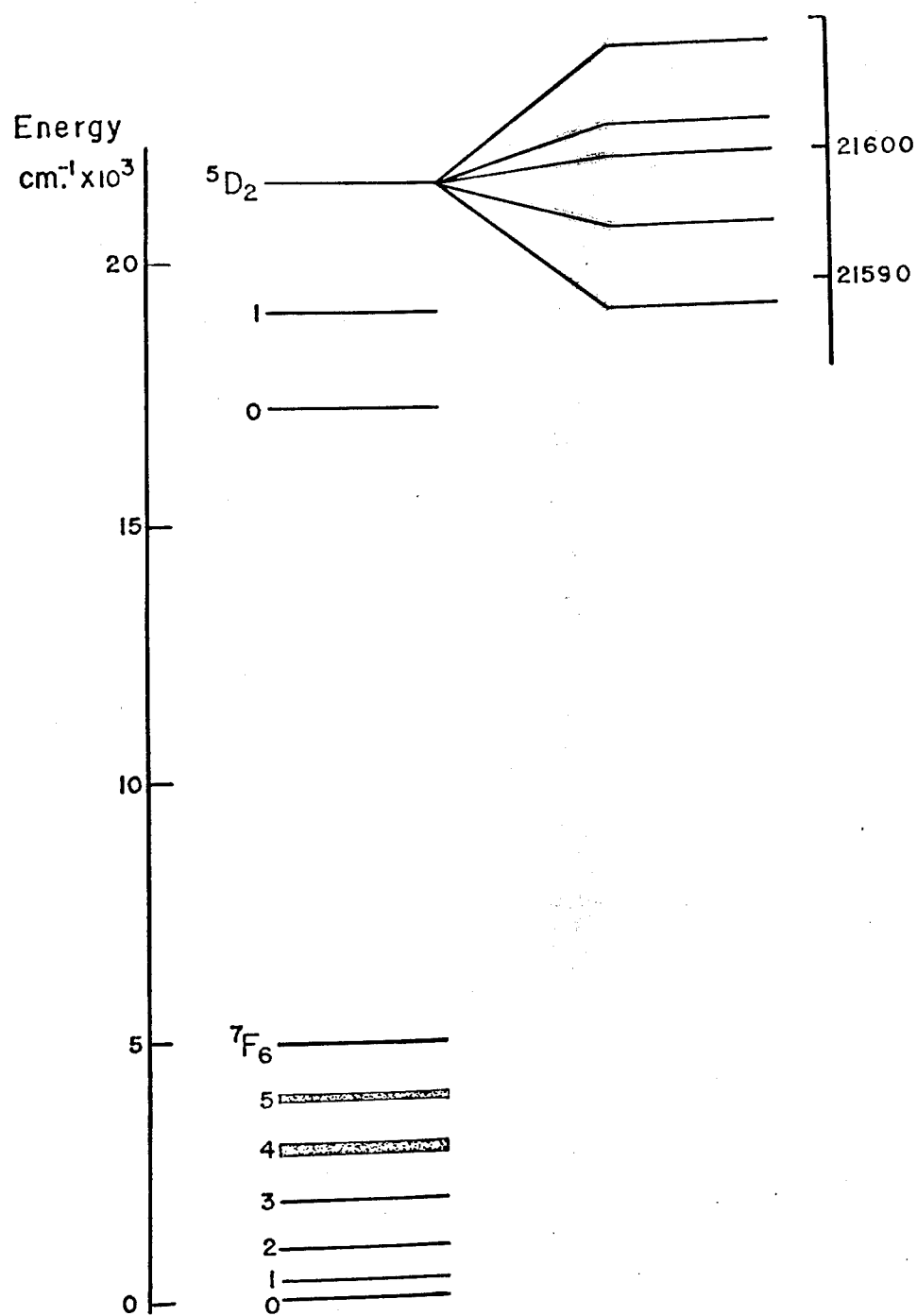
FIG. 6 shows the electronic energy level for a typical rare earth ion and small additional splittings of each of the levels into a manifold of levels that occurs when the rare earth is introduced as a dopant into the lattice.

The technique uses the sharp lines characteristic of ionic spectra from unfilled inner orbitals. The electronic energy levels of the unfilled $4f^n$ orbitals of the free rare earth ion $Eu^{3+}$ are sketched in FIG. 6. When this ion is introduced as a dopant into a crystalline lattice, the strong fields of the lattice split each of the individual levels shown into a manifold of crystal field levels. The pattern of splitting depends upon the strength and symmetry of the local fields that the ion experiences. The splittings are not large in this particular example because the $4f^n$ orbitals that are active in the spectroscopic transitions are well shielded by the outer $5s^2\ 5p^6$ orbitals. Typical splittings are shown in FIG. 6 as an enlarged view of the $^5D_2$ manifold. These splittings are easily observable with a moderate resolution instrument. They are also very narrow in energy because of the same shielding effect from the outer orbitals.

At very low temperatures, only the bottom level of the $4f^n$ configuration will be appreciably populated (the $^7F_o$ level in FIG. 6). Absorption transitions can occur to each of the crystal field levels in the upper manifolds. Once excited, a rare earth can relax either by fluorescence or by non-radiative dissipation of the energy into lattice phonons. If the difference in energy between an excited level and the level immediately below it is sufficiently small that it can be absorbed by less than about 5 lattice phonons, the level will relax non-radiatively to the next lowest level. If the energy gap is large, however, fluorescence will be the most efficient process. The $^5D_o$ level of FIG. 6 is a very efficient fluorescent level. Fluorescence transitions can be observed from this level to all of the $^7F_J$ manifolds. The $^5D_o$ manifold fluorescence is produced by excitation of the $^5D_1$, $^5D_2$, etc. manifolds which relax non-radiatively to the $^5D_o$ manifold.

Whenever such an ion is introduced into an arbitrary host lattice as a dopant, there can be a number of possible crystallographic sites. Each of the sites will have a different set of crystal field levels associated with it since the local fields will be quite different. If the crystal field splitting pattern is considered to be a "fingerprint" of the site that produces it, one can observe the behavior of that site as the host lattice is modified by monitoring the spectroscopic transitions between the crystal field levels. The ion is therefore acting as a probe of the immediate crystallographic environment surrounding it. A severe difficulty arises, however, when one attempts to use such ions as probes in situations of practical interest. Most interesting materials have a number of possible crystallograhic sites. The spectra of each individual site overlaps the spectra of every other one and the net result is a complex, composite spectra that is very difficult or impossible to interpret or use.

We have found that the solution of this difficulty is to use a narrow-band coherent light source tuned to a specific absorption line of a specific site in the crystal. Since the absorption lines are sharp and generally fall at different wavelengths for different sites, a single site can be selectively excited by tuning a laser to that absorption line. If that site does not transfer its energy to a different site, the resulting fluorescence spectrum will be characteristic of that site alone. Conversely, if a specific fluorescence line of a specific site is monitored continuously as a dye laser is scanned over all possible excitation wavelengths, a single excitation spectrum can be obtained. The result is a dramatic simplification of the spectrum. This technique has been evaluated extensively in single crystals of $CaF_2:Er^{3+}$ [1], as well as in $BaSO_4:Eu^{3+}$ in the described illustration. It has been found that energy transfer between sites did not occur and selective excitation of single sites can always be obtained as long as there is no absorption line overlap with other sites. The latter situation is not generally a problem because there are so many possible absorption lines that one can almost always be found that does not overlap.

[1] D. R. Tallant and J. C. Wright, J. Chem. Physics 63, 2074 (1975).

The basic concept underlying the analytical method of this invention is to incorporate an ion with unfilled inner orbitals in a precipitation of some host lattice to act as a probe into that lattice. If other ions co-precipitate along with the probe ion, there will be a modification of the crystal field experienced by the probe ion, because of the new ion introduced into the lattice, and one will observe a new site in the spectrum of the precipitate. The fluorescence intensity from the site is related to the original concentration of the foreign ion in the original solution. Although one would expect a number of different sites to be formed in a process as complex as a precipitation, the technique of selective excitation can excite the particular site of interest with a high degree of specificity. The sensitivity is also very high with the particular system described. Calculations indicate that the procedure of this invention is applicable even when only $8 \times 10^{+5}$ ions are present in any particular site.

Briefly described, the components required to be present for practice of the invention include a probe, a host, and the unknown to be determined. It is possible that any two or even all three of these entities could be the same ion. In the preceding example, all three were different. The $PO_4^{---}$ was the unknown, the barium sulphate was the host, and the europium ion represented the probe. In the situation where a rare earth metal compound is also used to form the precipitate, then the single compound can function in the procedure both as the probe and as the host with which the unknown would come down as a co-precipitate in the lattice to modify the energy level of the rare earth. This situation can be illustrated in the detection of chloride ions ($Cl^-$) with europium in solution to which a large amount of fluoride is added to precipitate europium fluoride as the host with co-precipitation of chloride ion, even when present in trace amounts. The unknown and the host could also be the same. This could be illustrated by adding a sodium salt to a sulfate containing solution. Evaporation of the resulting solution would produce crystals of $Na_2SO_4$ as the $Na_2SO_4$ precipitates. A probe such as $Eu^{3+}$ could be added to the original solution to sense the presence of the $Na_2SO_4$ lattice and reflect through the fluorescence intensity the concentration of sulfate originally present.

Thus the essential components of the analysis method of this invention are a probe element that either fluoresces or absorbs light, which fluorescence or absorption wavelength is modified by the presence of an unknown anion or cation, when the probe element and the unknown are confined near each other in an organized solid structure (crystal), and a tuneable light source which can be used to interrogate the various known absorption sites of the probe species. The intensity of fluorescence is a function of the concentration of the unknown species. The unknown, the host crystal, and the probe can all be different or the same chemical species.

The probe is usually related to ions that have unfilled inner orbitals and exhibit sharp lines in its spectrum when placed into a crystalline lattice. Differences in the energy levels caused by different crystallographic sites can be detected and analyzed in accordance with the procedure of this invention. Probes which are not protected by outer orbitals do not exhibit sharp line spectra.

Representative of the materials which can be used as probes in the practice of this invention are the rare earth metals, transition metals and actinides, such as the ions of $Sm^{3+}$, $Eu^{3+}$, $Tb^{3+}$, $Ho^{3+}$, $Er^{3+}$, $Cr^{3+}$, $V^{3+}$, $Mn^{2+}$, $Os^{3+}$, $U^{3+}$, and $Pu^{3+}$.

Representative of the materials which can be used to form the host lattice are $SrSO_4$, $PbSO_4$, $CaSO_4$, $CaWO_4$, $Pb_3(AsO_4)_2$, $Ba_3(AsO_4)_2$, $Ba_3(PO_4)_2$, $Na_2SO_4$, $NaCl$, $NaSCN$, $CaF_2$, $BaF_2$, lanthanum oxalate, strontium oxalate, and the like.

Representative of the common anions that can be analyzed in accordance with the practice of the invention are the halogens, such as fluorine, bromine, chlorine and iodine, common anions such as phosphate, sulfate, nitrate, carbonate and the like, and many of the common cations which affect the energy levels of the light responsive probe ion.

It will be understood that changes may be made in the details of formulation and operation without departing from the spirit of the invention, especially as defined in the following claims.

I claim:

1. A method for analysis of cations and anions comprising incorporating said ions in a crystalline lattice containing ions of a probe which fluoresces upon excitation and which experiences a modification in energy level when said ions to be analyzed differ from that of the probe, exciting the probe ion with a tuneable narrow-band source of coherent light, and monitoring the fluorescence from the excited probe ion to analyze for sites in the spectrum to determine presence of the unknown cations or anions and the intensity of fluorescence thereof for determining the amount of said unknown anions or cations.

2. The method as claimed in claim 1 in which the ions to be analyzed are precipitated from solution with the probe for inclusion in the precipitated crystalline lattice.

3. The method as claimed in claim 1 in which the crystalline lattice containing the ions to be analyzed comprises a solid solution of the ions to be analyzed with the probe.

4. The method as claimed in claim 1 in which the tuneable coherent light source is a nitrogen laser excited dye laser.

5. The method as claimed in claim 1 in which the probe comprises ions which have unfilled inner orbitals and protective outer orbitals and which have well-defined energy levels that produce sharp line spectra.

6. The method as claimed in claim 1 in which the probe ions are of a metal selected from the group consisting of rare earth metals, transition metals, and metals of the actinide group.

7. The method as claimed in claim 1 in which the unknown ions to be analyzed for include halogen, phosphates, sulfates and other anions.

8. The method as claimed in claim 1 in which the amount of the unknown ion in solution is measurable from the intensity of the fluorescence resulting from excitation of the co-precipitate.

9. The method as claimed in claim 1 in which the spectrum is monitored by comparison with a standard calibrated spectrum for the unknown ion to determine the presence and the amount thereof.

10. The method as claimed in claim 1 in which the ions to be analyzed with the probe are incorporated in the crystalline lattice by co-precipitation.

11. The method as claimed in claim 10 in which the co-precipitate is formed by precipitation from solution of the probe ions and ions of the unknown by the addition of a host which causes co-precipitation of the probe ions and ions of the unknown.

12. The method as claimed in claim 11 in which, when the host includes the ions of the probe, the host and probe can be one and the same.

13. The method as claimed in claim 11 in which ions in the host and the ions to be analyzed may be one and the same while the probe is different.

14. The method as claimed in claim 11 in which the ions of the probe and the ions to be analyzed may be the same while the host is different.

15. The method as claimed in claim 11 in which the ions of the probe, ions in the host and the ions to be analyzed are one and the same.

* * * * *